United States Patent
Tanaka et al.

(10) Patent No.: US 6,608,233 B2
(45) Date of Patent: Aug. 19, 2003

(54) PROCESS FOR PRODUCTING BIS(4-HYDROXY-3-NITROPHENYL) COMPOUND

(75) Inventors: Eiichi Tanaka, Saitama (JP); Masaki Fujimoto, Saitama (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 0 days.

(21) Appl. No.: 10/257,218

(22) PCT Filed: Apr. 23, 2001

(86) PCT No.: PCT/JP01/03434

§ 371 (c)(1),
(2), (4) Date: Oct. 10, 2002

(87) PCT Pub. No.: WO01/81293

PCT Pub. Date: Nov. 1, 2001

(65) Prior Publication Data

US 2003/0055288 A1 Mar. 20, 2003

(30) Foreign Application Priority Data

Apr. 25, 2000 (JP) ............................. 2000-123430

(51) Int. Cl.$^7$ ............................. C07L 205/00
(52) U.S. Cl. ............................. 568/707; 568/30; 568/36; 568/39; 568/306; 568/586
(58) Field of Search ............................. 568/707, 306, 568/586, 30, 36, 39

(56) References Cited

U.S. PATENT DOCUMENTS

| 2,560,939 | A | * | 7/1951 | Faith |
| 2,615,052 | A | * | 10/1952 | Faith |
| 2,739,941 | A | * | 3/1956 | Chiddix |
| 3,563,950 | A | * | 2/1971 | Steinmann |
| 4,505,840 | A | * | 3/1985 | Kurkov |
| 4,978,808 | A | * | 12/1990 | Maruta |
| 5,028,728 | A | * | 7/1991 | Schneider |
| 5,151,488 | A | * | 9/1992 | Hutchings |

FOREIGN PATENT DOCUMENTS

| EP | 254990 | * | 2/1988 |
| EP | 0 254 990 | | 2/1988 |
| JP | 59-27950 | | 2/1984 |
| JP | 5-109546 | | 6/1984 |
| JP | 6-211752 | * | 8/1994 |
| JP | 11-106365 | * | 4/1999 |

* cited by examiner

Primary Examiner—Michael L. Shippen
(74) Attorney, Agent, or Firm—Nields & Lemack

(57) ABSTRACT

The present invention relates to a process for producing a bis(4-hydroxy-3-nitrophenyl) compounds, characterized by nitrating a bis(4-hydroxyphenyl) compound wherein two phenyl groups are bonded to each other directly or through an electron-donating bridging group, sulfoxide group, sulfone group or carbonyl group in an inert solvent using nitric acid under the condition of substantially free from any other acid. According to the process, the target compounds reduced in the content of trinitrates can be produced in high yield and further recrystallizing the compound easily gives in high yield a high-purity products suitable for use as a raw material of producing a heat-resistant polymer and so on because the content of a trinitro-substitued compound in that compound is low.

7 Claims, No Drawings

PROCESS FOR PRODUCTING BIS(4-HYDROXY-3-NITROPHENYL) COMPOUND

TECHNICAL FIELD

The present invention relates to a process for producing bis(4-hydroxy-3-nitrophenyl) compounds which are intermediate for producing polymers.

BACKGROUND ART

A bis(3-amino-4-hydroxyphenyl) compound obtained by reducing a bis(4-hydroxy-3-nitrophenyl) compound is an important intermediate since it becomes a material monomer for poly(benzoxazole) which is expected as photosensitive heat-resistant polymers for VLSI and highly heat-resistant polymers with high strength.

The following processes have been known as the processes for producing bis(4-hydroxyphenyl) compounds comprising two phenyl groups bonded to each other directly or through an electron donating bridging group.

In Polymer Letters vol. 7:185–191 (1969), 2,2-bis (4-hydroxyphenyl)propane is nitrated with nitric acid (sp. gr. 1.42) in a mixed solvent of acetic acid and benzene. A crude product is composed of a solid by filtration and a solid obtained by concentrating the filtrate. The yield is 72% of the theoretical amount. The crude product is recrystallized to obtain 2,2-bis(4-hydroxy-3-nitrophenyl)propane with high purity for a polymer material. According to the reference, it has been described that several times of recrystallization were required to yield those of the polymer material grade and that notice to avoid mononitration and trinitration is needed.

Also, Japanese Patent Laid-Open N.27950/1984 has described the method in which 4,4'-biphenol is nitrated with 70% nitric acid in large amounts of acetic acid. The crude product is obtained by filtration in a yield of 85%. 3,3-Dinitro-4,4'-dihydroxybiphenyl used for making polymers is obtained by recrystallization from acetic acid.

However, when the bis(4-hydroxyphenyl) compound such as 4,4'-biphenol and 2,2-bis(4-hydroxy-3-nitrophenyl) propane and the like in which two phenyl groups are bonded to each other directly or through the electron-donating bridging group is dinitrated in the presence of acetic acid in the methods known in the art, there is an issue that it is difficult to obtain a high-purity products in high yield because hazardous trinitrates are produced at about 5 to 10% as by-products, which are difficult to remove by purification. Also in these methods, nitric acid is used in amount of 2.5-fold or more based on the theoretical amount, and the large amount of solvent is usually necessary. Thus, there have been problems in industrial production in that costs for waste (by-product) disposal and solvent recovery become expensive.

On the other hand, as the process for producing 2,2-bis (4-hydroxy-3-nitrophenyl) hexafluoropropane by nitrating 2,2-bis(4-hydroxyphenyl)hexafluoropropane in which two phenyl groups are bonded to each other through an electron-withdrawing group, the method by nitrating in chloroform at a temperature from 15 to 25° C. using 50% of nitric acid in the absence of any other acid is specifically disclosed in Japanese Patent Laid-Open No.33353/1988. Since the bridging group is the electron-withdrawing group in 2,2-bis(4-hydroxyphenyl)hexafluoropropane, the reactivity of the compound is lower than that of the compound with the electron-donating group. Therefore, instead of no problem of the formation of trinitrates, nitration has been known in the presence of trifluoroacetic acid which is less available and requires careful handling in order to obtain in high yield. In the said Japanese Patent Laid-Open, it has been described that, since it was difficult to manufacture by this method using trifluoroacetic acid in the industrial scale, the above method was developed as the method for manufacturing in an industrial scale without the use of trifluoroacetic acid.

The present invention provides a nitration process wherein bis(4-hydroxyphenyl) compounds such as 4,4'-biphenol or 2,2-bis(4-hydroxy-3-nitrophenyl)propane comprising two phenyl groups bonded to each other directly or through an electron-donating bridging group, which is highly reactive and easily trinitrated is dinitrated with few production of trinitrate unlike conventional methods, to be able to obtain a target bis(4-hydroxy-3-nitrophenyl) compound in high yield such as approximately 90% after purification, as well as capable of manufacturing easily in an industrial scale.

DISCLOSURE OF THE INVENTION

As a result of the intensive study, the present inventors have found that a bis(4-hydroxy-3-nitrophenyl) compound can be given with high purity in high yield with small amount of by-products such as trinitrate and the like by nitration of a bis(4-hydroxyphenyl) compound comprising two phenyl groups bonded to each other directly or through an electron-donating group in an inert solvent substantially without any other acids but with nitric acid, preferably from 55 to 75% of nitric acid (by weight), and have completed the present invention.

That is, the present invention relates to:

(1) a process for producing bis(4-hydroxy-3-nitrophenyl) compounds, characterized by nitrating bis(4-hydroxyphenyl) compounds wherein two phenyl groups are bonded to each other directly or through an electron-donating group, sulfoxide group, sulfone group or carbonyl group in an inert solvent using nitric acid under the condition of substantially free from any other acid;

(2) the process for producing the bis(4-hydroxy-3-nitrophenyl) compounds described in the above (1) wherein the bis(4-hydroxy-3-nitrophenyl) compounds are represented by the formula (1):

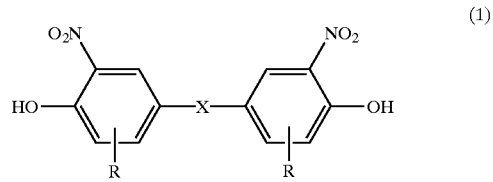

(1)

wherein X represents methylene, 2,2-isopropyrene, oxy, thio, sulfoxide, sulfone, carbonyl or a direct bond; each R may be a different substituent and represents a hydrogen atom, an alkyl group which may be substituted with halogen, an alkoxy group which may be substituted with halogen, an acyloxy group, a carboxyl group, an alkyloxycarbonyl group, a carbamoyl group, an amino group which may be substituted with a mono- or di-(C1 to C6) alkyl group, a hydroxy group or a halogen atom;

(3) the process for producing the bis(4-hydroxy-3-nitrophenyl) compounds described in the above (1) or (2) wherein a concentration of nitric acid is from 10 to 95%;

(4) the process for producing the bis(4-hydroxy-3-nitrophenyl) compounds described in the above (3) wherein a reaction temperature is from −15 to 35° C.;

(5) the process for producing the bis(4-hydroxy-3-nitrophenyl) compounds described in the above (4) wherein the solvent is aliphatic or aromatic chlorinated hydrocarbon;

(6) the process for producing the bis(4-hydroxy-3-nitrophenyl) compounds described in the above (5) wherein the bis(4-hydroxy-3-nitrophenyl) compounds are 2,2-bis(4-hydroxy-3-nitrophenyl)propane, di(4-hydroxy-3-nitrophenyl)ether or 4,4'-dihydroxy-3,3'-dinitrobiphenyl; and (7) the process for producing the bis(4-hydroxy-3-nitrophenyl) compounds described in the above (6) wherein nitration is carried out at the reaction temperature of from −5° C. to 10° C. using an aqueous solution of nitric acid of which concentration is from 55% to 85%.

BEST MODE FOR CARRYING OUT THE INVENTION

The process for the production of the present invention is described below in detail.

The electron-donating bridging group of the present invention is not especially limited as long as it is the electron-donating bridging group, and can include, for example, branched or unbranched alkylene of from 1 to 6 carbons, and more preferably alkylene of from 1 to 4 carbons, oxy, thio and the like.

In the formula (1), X represents methylene, 2,2-isopropyrene, oxy, thio, sulfoxide, sulfone, carbonyl or a direct bond of the phenyl groups each other.

The alkyl group represented by R, which may be substituted with halogen (e.g., halogen-substituted or unsubstituted alkyl group of from 1 to 10 carbons) is preferably an alkyl group which may be substituted with fluorine (e.g., fluorine-substituted or unsubstituted alkyl group of from 1 to 6 carbons). Its specific examples include methyl, ethyl, n-propyl, isopropyl, n-butyl, isobutyl, tert-butyl, pentyl, hexyl, trifluoromethyl, perfluoroethyl, hexafluoropropyl and the like. The alkoxy group which may be substituted with halogen (e.g., halogen-substituted or unsubstituted alkoxy group of from 1 to 10 carbons) is preferably the alkoxy group which may be substituted with fluorine (e.g., from 1 to 6 fluorine-substituted or unsubstituted alkoxy group of from 1 to 6 carbons). Its specific examples include methoxy, ethoxy, propoxy, butoxy, pentyloxy, hexyloxy, trifluoromethoxy, perfluoroethoxy, hexafluoropropoxy and the like. The acyloxy group includes, for example, the acyloxy group of from 1 to 10 carbons, which may be substituted with halogen. Its specific examples include acetoxy, propionyloxy, butyryloxy, trifluoroacetoxy and the like. The alkyloxycarbonyl group includes, for example, the alkyloxycarbonyl group of from 1 to 10 carbons, which may be substituted with halogen and so on. Its specific examples include methoxycarbonyl, ethoxycarbonyl, propoxycarbonyl, butoxycarbonyl and the like. The carbamoyl group includes the carbamoyl group which may be substituted with an alkyl group of from 1 to 10 carbons. Its specific examples include carbamoyl, methylcarbamoyl, ethylcarbamoyl, n-propylcarbamoyl, n-butylcarbamoyl, dimethylcarbamoyl, diethylcarbamoyl, di-n-propylcarbamoyl, di-n-butylcarbamoyl and the like, and preferably unsubstituted carbamoyl group. The amino group which maybe substituted with mono- or di(C1 to C6) alkyl group includes unsubstituted amino group, monomethylamino group, di-propylamino group and the like. Also, halogen atoms include fluorine, chlorine, bromine and iodine, and fluorine is preferred. Two R may be each different, but it is preferable that they are the same.

The (4-hydroxy-3-nitrophenyl) compounds represented by the above formula (1), given by the process for the production of the present invention include bis(4-hydroxy-3-nitro)methanes, 2,2-bis(4-hydroxy-3-nitrophenyl)propanes, di(4-hydroxy-3-nitrophenyl)ethers, bis(4-hydroxy-3-nitrophenyl)sulfides, bis(4-hydroxy-3-nitrophenyl)sulfoxides, bis(4-hydroxy-3-nitrophenyl)sulfones, bis(4-hydroxy-3-nitrophenyl)ketones, 4,4'-dihydroxy-3,3'-dinitrobiphenyls.

Specific examples of bis(4-hydroxy-3-nitrophenyl)methanes include bis(4-hydroxy-3-nitro-5-or 6-R)methane substituted with the aforementioned R at the 5 or 6 position such as bis(4-hydroxy-3-nitrophenyl)methane, bis(4-hydroxy-3-nitro-5-methylphenyl)methane, bis(4-hydroxy-3-nitro-5-trifluoro-methylphenyl)methane, bis(4-hydroxy-3-nitro-5-methoxyphenyl)methane, bis(4-hydroxy-3-nitro-6-methoxyphenyl)methane, bis(4-hydroxy-3-nitro-5-acetoxyphenyl)methane, bis(4-hydroxy-3-nitro-5-methoxycarbonylphenyl)methane, bis(4-hydroxy-3-nitro-5-diethylcarbamoylphenyl)methane, bis(4-hydroxy-3-nitro-5-fluorophenyl)methane and the like.

Specific examples of 2,2-bis(4-hydroxy-3-nitrophenyl)propanes include bis(4-hydroxy-3-nitro-5 or 6-R)propane substituted with the aforementioned R at the 5 or 6 position, such as 2,2-bis(4-hydroxy-3-nitrophenyl)propane, 2,2-bis(4-hydroxy-3-nitro-5-ethylphenyl)propane, 2,2-bis(4-hydroxy-3-nitro-5-trifluoromethylphenyl)propane, 2,2-bis(4-hydroxy-3-nitro-5-methoxyphenyl)propane, 2,2-bis(4-hydroxy-3-nitro-5-acetoxyphenyl)propane, 2,2-bis(4-hydroxy-4-nitro-6-acetoxyphenyl)propane, 2,2-bis(4-hydroxy-3-nitro-5-ethoxycarbonylphenyl)propane, 2,2-bis(4-hydroxy-3-nitro-5-methylcarbamoylphenyl)propane, 2,2-bis(4-hydroxy-3-nitro-5-fluorophenyl)propane and the like. Among them, 2,2-bis(4-hydroxy-3-nitrophenyl)propane is especially preferred.

Specific examples of di(4-hydroxy-3-nitrophenyl)ethers include di(4-hydroxy-3-nitro-5 or 6-R)ether substituted with the aforementioned R at the 5 or 6 position, such as di(4-hydroxy-3-nitrophenyl)ether, di(4-hydroxy-3-nitro-6-methylphenyl)ether, di(4-hydroxy-3-nitro-5-carboxyphenyl)ether, di(4-hydroxy-3-nitro-5-trifluoromethylphenyl)ether, di(4-hydroxy-3-nitro-6-chlorophenyl)ether and the like. Among them, di(4-hydroxy-3-nitrophenyl)ether is especially preferred.

Specific examples of bis(3-nitro-4-hydroxyphenyl)sulfides include di(4-hydroxy-3-nitro-5 or 6-R)sulfide and the like substituted with the aforementioned R at the 5 or 6 position, such as bis(3-nitro-4-hydroxyphenyl)sulfide, bis(3-nitro-4-hydroxy-5-isobutylphenyl)sulfide, bis(3-nitro-4,5-dihydroxyphenyl)sulfide, bis(3-nitro-4-hydroxy-5-(N-methylamino)phenyl)sulfide, bis(3-nitro-4-hydroxy-5-bromophenyl)sulfide and the like.

Specific examples of bis(3-nitro-4-hydroxyphenyl)sulfones include di(4-hydroxy-3-nitro-5 or 6-R)sulfone and the like substituted with the aforementioned R at the 5 or 6 position of bis(4-hydroxy-3-nitro-5 or 6-R)sulfone and the like, such as bis(3-nitro-4-hydroxyphenyl)sulfone, bis(3-nitro-4-hydroxy-5-isobutylphenyl)sulfone, bis(3-nitro-4-hydroxy-6-propanoylphenyl)sulfone, bis(3-nitro-4-hydroxy-5-(N,N-dipropylamino)phenyl)sulfone and the like.

Specific examples of bis(3-nitro-4-hydroxyphenyl) ketones include di(4-hydroxy-3-nitro-5 or 6-R)ketone and the like substituted with the aforementioned R at the 5 or 6 position, such as bis(3-nitro-4-hydroxy-6-methylphenyl) ketone, bis(3-nitro-4-hydroxy-5-ethoxyphenyl)ketone, bis (3-nitro-4-hydroxy-5-acetylphenyl)ketone, bis(3-nitro-4-hydroxy-5-isopropylphenyl)ketone, bis(3-nitro-4-hydroxy-6-methylphenyl)ketone, bis(3-nitro-4-hydroxy-5-(N,N-dipropylamino)phenyl)ketone and the like.

Specific examples of 4,4'-dihydroxy-3,3'-dinitrobiphenyls include biphenyl substituted with the aforementioned R at the 5 or 6 position, such as 4,4'-dihydroxy3,3'-dinitrobiphenyl, 4,4'-dihydroxy-3,3'-dinitro-5,5'-difluorobiphenyl, 4,4'-dihydroxy-3,3'-dinitro-5,5-ditrifluoromethylbiphenyl, 4,4'-dihydroxy-3,3'-dinitro-5,5'-dimethoxycarbonylbiphenyl, 4,4'-dihydroxy-3,3'-dinitro-6,6'-dimethylbiphenyl and the like. Among them, 4,4'-dihydroxy-3,3'-dinitrobiphenyl is especially preferred.

The bis(4-hydroxyphenyl) compounds which are the starting compound used for the process for the production of the present invention correspond to the target compounds in which the nitro group is eliminated from the 3 position of the bis(4-hydroxy-3-nitrophenyl) compound of the target compound, and for example, is the compound in which the nitro group is not bonded in the bis(4-hydroxy-3-nitrophenyl) compound represented by the above formula (1). That is, the starting compounds for producing bis(4-hydroxy-3-nitrophenyl)methanes are the corresponding 2,2-bis(4-hydroxyphenyl)methanes, the starting compounds for producing 2,2-bis(4-hydroxy-3-nitrophenyl)propanes are the corresponding 2,2-bis(4-hydroxy-phenyl)propanes, the starting compounds for producing di(4-hydroxy-3-nitrophenyl)ethers are the corresponding di(4-hydroxyphenyl)ethers, the starting compounds for producing bis(4-hydroxy-3-nitrophenyl)sulfides are the corresponding bis(4-hydroxyphenyl)sulfides, the starting compounds for producing bis(4-hydroxy-3-nitrophenyl)sulfoxides are the corresponding bis(4-hydroxyphenyl)sulfoxides, the starting compounds for producing bis(4-hydroxy-3-nitrophenyl) sulfones are the corresponding bis(4-hydroxyphenyl) sulfones, the starting compounds for producing bis(4-hydroxy-3-nitrophenyl)ketones are the corresponding bis(4-hydroxyphenyl)ketones, and the starting compounds for producing 4,4'-dihydroxy-3,3'-dinitrobiphenyls are the corresponding 4,4'-dihydroxybiphenyls.

These compounds which are the starting compounds of the process for the production of the present invention can be readily available industrially or can be easily obtained by the techniques conventionally known in the art.

Nitric acid used in the present invention is an aqueous solution of nitric acid at a concentration of from 10 to 95% (by mass: the same hereinafter unless otherwise specified), and nitric acid for the industry on sale is used as such or by being diluted with water. Preferable concentration of nitric acid solution is 55% or more, more preferably 60% or more and 85% or less, more preferably 75% or less. The amount of nitric acid to be used is usually in the range of from 1.7 to 3 moles, preferably around the theoretical amount, for example, 1.8 moles or more, more preferably 1.9 moles or more and 2.4 moles or less, more preferably 2.3 moles or less, and still more preferably 2.2 moles or less based on 1 mole of the bis(4-hydroxyphenyl) compound.

The reaction temperature according to the present invention is usually from −15 to 35° C., preferably −5° C. or above and 10° C. or below, and more preferably 5° C. or below.

The process for the production of the present invention is usually carried out in the presence of an inert solvent. The inert solvents are preferably aliphatic or aromatic chlorinated hydrocarbons. Specific examples of the usable aliphatic chlorinated hydrocarbons can exemplify aliphatic hydrocarbons having from 1 to 3 carbons substituted with from 1 to 6 chlorine atoms, preferably from 2 to 4 chlorine atoms such as dichloromethane, chloroform, carbon tetrachloride, 1,2-dichloroethane, 1,1-dichloroethane, 1,1,1-trichloroethane and the like. Similarly, examples of aromatic chlorinated hydrocarbons can exemplify benzenes substituted with from 1 to 3 chlorine atoms, such as monochlorobenzene, orthodichlorobenzene, 1,2,3-trichlorobenzene and the like. Among them, dichloromethane, 1,2-dichloroethane, monochloro benzene or orthodichlorobenzene is more preferred. The amount of the solvent used for the reaction is usually from 3 to 20 folds (mass ratio) and preferably from about 5 to 10 folds based on the amount of the bis(4-hydroxyphenyl) compound.

In the reaction manipulation method for the process of the production of the present invention, the bis(4-hydroxyphenyl) compounds are dissolved or dispersed in the inert solvent such as dichloromethane with stirring and the given amount of nitric acid is poured by small and small therein with keeping the given temperature. The pouring time is usually from 0.5 to 20 hours, and preferably from 3 to 10 hours. After pouring nitric acid, stirring is continued for 0.5 to 10 hours with keeping the given temperature to complete the reaction. Water is added to the reaction mixture to separate an organic layer from an aqueous layer, and the organic layer is washed with a diluted alkali aqueous solution until becoming neutral. Subsequently, the solvent is distilled off to obtain the crude product. When the reaction mixture is in suspension, after adding water, the mixture is filtrated and the filtrated cake is washed with the diluted alkali aqueous solution followed by water until the filtrate becomes neutral to obtain the crude product.

At the reaction, dispersants may be added to improve mixing and fluidity. Usable dispersants can include alkylbenzene sulfonate, naphthalene sulfonate, formalin condensate, acrylic acid-maleic acid copolymer, and condensed phosphate.

The crude product can be purified by recrystallizing from alcohols such as methanol, ethanol, isopropanol and the like, ethers such as ethyleneglycolmonoethyl ether, tetrahydrofuran, and the like, ketones such as 2-butanone, 3-methyl-2-butanone, and the like, non-proton polar solvents such as dimethylformamide, dimethylacetoamide, N-methyl-2-pyrrolidone and the like.

EXAMPLES

Next, the present invention is described in more detail by examples, but the invention is not limited to these examples.

Example 1

Production of 4,4'-dihydroxy-3,3'-dinitrobiphenyl

Into a 200 ml four-neck flask fitted with a thermometer and stirrer, 120 ml of dichloromethane and 18.6 g of 4,4'-dihydroxybiphenyl (0.10 mol) were added, and 19.8 g of 70% of an aqueous solution of nitric acid by weight (0.22 mol)(d=1.42) was poured over 3 hours with cooling and keeping the temperature at from 0 to 5° C. The mixture was stirred for additional 3 hours at the same temperature to complete the reaction. The reaction products were filtrated and the filtrated cake was thoroughly washed with an aqueous solution of diluted sodium hydrogen carbonate followed by water. Then, 27.2 g of crude 4,4'-dihydroxy-3, 3'-dinitrobiphenyl was obtained in a yellow brown crystal by drying. (98% based on the theoretical yield, HPLC analysis (area %): 4,4'-dihydroxybiphenyl 0.4%, mononitro-substituted compound 1.5%, dinitro-substituted compound 98.0% and trinitro-substituted compound 0.1% or less). This was recrystallized from dimethylformamide to obtain 24.4 g of 4,4'-dihydroxy-3,3'-dinitrobiphenyl (purified yield 90%, purity: HPLC 99.8%)

Example 2

Production of 2,2-bis(4-hydroxy-3-nitrophenyl) propane

Into a 500 mL four-neck flask fitted with a thermometer and stirrer, 170 ml of dichloromethane and 23.0 g of 2,2-bis(4-hydroxyphenyl)propane (bisphenol A) (0.10 mol) were added, and 20.8 g of 70% of an aqueous solution of nitric acid by weight (0.23 mol) (d=1.42) was poured over 3 hours with cooling and keeping the temperature at from 0 to 5° C. The mixture was stirred for additional 4 hours at the same temperature, and subsequently water was added and stirred to remove acids into the aqueous layer. Then, the organic layer was separated and washed with the aqueous solution of sodium hydrogen carbonate until becoming neutral. When dichloromethane was distilled off, a viscous liquid was obtained, which was cooled to obtain 30.2 g of crude 2,2-bis(4-hydroxy-3-nitrophenyl)propane in crystal. (95% based on the theoretical yield, HPLC analysis (area %): bisphenol A 0.8%, mononitro-substituted compound 2.0%, dinitro-substituted compound 96.5%, trinitro-substituted compound 0.5%). This was recrystallized from methanol to obtain 27.7 g of 2,2-bis(4-hydroxy-3-nitrophenyl)propane. (purified yield 92%, purity: HPLC 99.8%)

Comparative Example 4,4'-Dihydroxybiphenyl was nitrated by the same manipulation as that in Example 1, except that dichloromethane was displaced with acetic acid. By filtrating, 26.4 g of a crystal of crude 4,4'-dihydroxy-3,3'-dinitrophenyl was obtained (95.5% based on the theoretical yield, HPLC analysis (area %): mononitro-substituted compound 3.0%, dinitro-substituted compound 82.1%, trinitro-substituted compound 8.7%).

INDUSTRIAL APPLICABILITY

According to the process for the production of the present invention, the bis(4-hydroxy-3-nitrophenyl) compounds comprising two phenyl groups bonded to each other directly or through the electron-donating bridging group can be produced in a high yield with extremely less content of hazardous trinitrate, and those suitable for raw materials (intermediates) of heat-resistant polymers with high purity can be readily given in a high yield by recrystallization. Thus, the bis(4-hydroxy-3-nitrophenyl) compound can be obtained with high purity in a high yield.

What is claimed is:

1. A process for producing bis(4-hydroxy-3-nitrophenyl) compounds characterized by nitrating a bis(4-hydroxyphenyl) compound comprising two phenyl groups bonded to each other directly or through an electron-donating bridging group, sulfoxide, sulfone or carbonyl group using nitric acid in an inert solvent under the condition of the substantially free from any other acid.

2. The process for producing the bis(4-hydroxy-3-nitrophenyl) compounds according to claim 1 wherein the bis(4-hydroxy-3-nitrophenyl) compounds are represented by the formula (1):

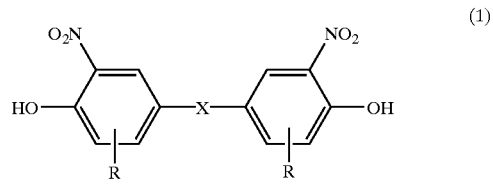

wherein X represents methylene, 2,2-isopropyrene, oxy, thio, sulfoxide, sulfone, carbonyl or a direct bond, and each R may be a different substituent and represents hydrogen, an alkyl group which may be substituted with halogen, an alkoxy group which may be substituted with halogen, an acyloxy group, a carboxyl group, an alkyloxycarbonyl group, a carbamoyl group, an amino group which may be substituted with mono- or di-(C1 to C6) alkyl group, a hydroxy group or a halogen atom.

3. The process for producing the bis(4-hydroxy-3-nitrophenyl) compounds according to claim 1 or 2, wherein a concentration of nitric acid is from 10 to 95%.

4. The process for producing the bis(4-hydroxy-3-nitrophenyl) compounds according to claim 3, wherein a reaction temperature is from −15 to 35° C.

5. The process for producing the bis(4-hydroxy-3-nitrophenyl) compounds according to claim 4, wherein the solvent is aliphatic or aromatic chlorinated hydrocarbon.

6. The process for producing the bis(4-hydroxy-3-nitrophenyl) compounds according to claim 5, wherein the bis(4-hydroxy-3-nitrophenyl) compounds are 2,2-bis(4-hydroxy-3-nitrophenyl) propane, di(4-hydroxy-3-nitrophenyl) ether or 4,4'-dihydroxy-3,3'-dinitrophenyl.

7. The process for producing the bis(4-hydroxy-3-nitrophenyl) compounds according to claim 6, wherein nitration is carried out at the reaction temperature of from −5° C. to 10° C. using an aqueous solution of nitric acid of which concentration is from 55% to 85%.

* * * * *